United States Patent
Hwang et al.

(10) Patent No.: US 10,227,668 B2
(45) Date of Patent: Mar. 12, 2019

(54) METHOD FOR PREPARING FRUCTOSE OR XYLULOSE FROM BIOMASS CONTAINING GLUCOSE OR XYLOSE USING BUTANOL, AND METHOD FOR SEPARATING THE SAME

(71) Applicant: KOREA RESEARCH INSTITUTE OF CHEMICAL TECHNOLOGY, Daejeon (KR)

(72) Inventors: Dong Won Hwang, Daejeon (KR); Pravin Pandharinath Upare, Daejeon (KR); Young Kyu Hwang, Daejeon (KR); In Taek Hwang, Daejeon (KR); Jong San Chang, Daejeon (KR); Do Young Hong, Yongin-si (KR); U Hwang Lee, Daejeon (KR)

(73) Assignee: Korea Research Institute of Chemical Technology, Daejeon (KR)

(*) Notice: Subject to any disclaimer, the term of this patent is extended or adjusted under 35 U.S.C. 154(b) by 64 days.

(21) Appl. No.: 15/635,060

(22) Filed: Jun. 27, 2017

(65) Prior Publication Data
US 2018/0002769 A1 Jan. 4, 2018

(30) Foreign Application Priority Data

Jul. 1, 2016 (KR) .................. 10-2016-0083679
Apr. 10, 2017 (KR) .................. 10-2017-0046119

(51) Int. Cl.
| | |
|---|---|
| C13K 1/10 | (2006.01) |
| C13K 11/00 | (2006.01) |
| C13K 13/00 | (2006.01) |
| C13K 3/00 | (2006.01) |
| B01J 27/236 | (2006.01) |
| B01J 29/40 | (2006.01) |
| B01J 29/70 | (2006.01) |
| B01J 37/00 | (2006.01) |
| B01J 37/02 | (2006.01) |
| B01J 37/03 | (2006.01) |
| B01J 37/04 | (2006.01) |
| B01J 37/06 | (2006.01) |
| B01J 37/08 | (2006.01) |
| C07D 307/50 | (2006.01) |
| C07H 1/00 | (2006.01) |
| C07H 3/02 | (2006.01) |

(52) U.S. Cl.
CPC ............ *C13K 11/00* (2013.01); *B01J 27/236* (2013.01); *B01J 29/40* (2013.01); *B01J 29/7007* (2013.01); *B01J 37/009* (2013.01); *B01J 37/0236* (2013.01); *B01J 37/031* (2013.01); *B01J 37/04* (2013.01); *B01J 37/06* (2013.01); *B01J 37/08* (2013.01); *C07D 307/50* (2013.01); *C07H 1/00* (2013.01); *C07H 3/02* (2013.01); *C13K 3/00* (2013.01); *C13K 13/00* (2013.01); *C13K 13/002* (2013.01); *C13K 13/007* (2013.01)

(58) Field of Classification Search
None
See application file for complete search history.

(56) References Cited

U.S. PATENT DOCUMENTS

| | | | | |
|---|---|---|---|---|
| 3,704,168 A | * | 11/1972 | Hara et al. ............. | C08B 37/00 127/58 |
| 4,643,773 A | * | 2/1987 | Day .................... | C13K 11/00 127/30 |
| 4,888,060 A | * | 12/1989 | Niekamp .............. | C13K 3/00 127/60 |
| 2013/0072675 A1 | * | 3/2013 | Boutet ................. | C07H 1/06 536/127 |
| 2016/0130292 A1 | | 5/2016 | McKay et al. | |

FOREIGN PATENT DOCUMENTS

| | | |
|---|---|---|
| CN | 102399202 | 4/2012 |
| EP | 2892907 | 6/1916 |
| WO | WO 2012/050625 | 4/2012 |

OTHER PUBLICATIONS

Janado et al., "Hydrophobic Nature of Sugars as Evidenced by their Differential Affinity for Polystyrene Gel in Aqueous Media" Journal of Solution Chemistry (1985) vol. 14 No. 12 pp. 891-902 (Year: 1985).*

Engasser et al., "Kinetic modeling of glucose and fructose dissolution in 2-methyl 2-butanol" *Biochemical Engineering Journal*, 2008, 42(2):159-165.

Extended European Search Report issued in European Patent Application No. 17178918.3, dated Apr. 10, 2018.

Moreau et al., "Isomerization of glucose into fructose in the presence of cation-exchanged zeolites and hydrotalcites," *Applied Catalysis A: Gen.*, 2000, 193:257-264.

Partial European Search Report issued in Corresponding European Application No. 17178918.3 dated Nov. 9, 2017.

Zhang, et al. (2012). "Conversion of D-xylose into furfural with mesoporous molecular sieve MCM-41 as catalyst and butanol as the extraction phase." *Biomass and Bioenergy*, 39, pp. 73-77.

Tewari, "Thermodynamics of Industrially-Important, Enzyme-Catalyzed Reactions" *Applied Biochemistry and Biotechnology*, 1990, 23: 187-203.

(Continued)

*Primary Examiner* — Eric Olson
(74) *Attorney, Agent, or Firm* — Norton Rose Fulbright US LLP

(57) ABSTRACT

The present invention relates to a method for preparing fructose or xylulose from biomass comprising glucose or xylose, and a method for separating a mixture of glucose and fructose and a mixture of xylose and xylulose.

17 Claims, 2 Drawing Sheets

(56) References Cited

OTHER PUBLICATIONS

Yu, et al., "Isomerization of glucose into fructose over Mg—Al hydrotalcite catalysts" *Catalysis Communications*, 2012, 29: 63-67.
Moliner, et al., "Tin-containing zeolites are highly active catalysts for the isomerization of glucose in water" *PNAS*, 2010, 107: 6164-6168.
Lima, et al., "Isomerization of D-glucose to D-fructose over metal-losilicate solid bases" *Applied Catalysis A: General*, 2008, 339: 21-27.

* cited by examiner

METHOD FOR PREPARING FRUCTOSE OR XYLULOSE FROM BIOMASS CONTAINING GLUCOSE OR XYLOSE USING BUTANOL, AND METHOD FOR SEPARATING THE SAME

CROSS REFERENCE TO RELATED APPLICATIONS

This application claims priority to and the benefit of Korean Patent Application No. 10-2016-0083679, filed Jul. 1, 2016, and Korean Patent Application No. 10-2017-0046119, filed Apr. 10, 2017. The contents of the referenced applications are incorporated into the present application by reference.

Technical Field

The present invention relates to a method for preparing fructose or xylulose from biomass containing glucose or xylose; and a method for separating a mixture of glucose and fructose and a mixture of xylose and xylulose.

Background Art

Amidst the worldwide controversy over developing alternative energy sources to overcome high oil prices, energy security, and the reinforcement of regulations on greenhouse gases, supply of biofuels is rapidly progressing as a fuel for the future. Biofuel refers to a sustainable energy source made from biomass in nature, and also refers to a useful alternative resource capable of overcoming the decrease of fossil fuel, that is, carbon resource. In addition, biomass is a concept including organic matters of organisms such as animals, plants, microorganisms, etc., and further, there are various kinds thereof such as all kinds of animals and plants as well as byproducts and waste produced from agriculture; food wastes; industrial wastes based on organisms; crops (energy crops) cultivated for the purpose of producing biofuels, etc. Biomass also commonly refers to renewable carbon resources including starches, celluloses, carbohydrates, proteins, organic municipal wastes, etc. Such biomass can be converted into biofuels in solid, liquid, or gaseous state because physical, chemical, and biological techniques are applied thereto, and further, is advantageous in that biomass will not be depleted, unlike fossil fuels. Accordingly, the foundation of sustainable novel green chemistry industry can be provided by producing useful chemical industrial materials from biomass. In particular, biochemical conversion technology, in which sugar substances provided from plant resources convert into various chemical substances, is recognized as a significant technical area that can be performed in the near future.

On the other hand, glucose (hexose) and xylose (pentose) are the cheapest and the most abundant biomass resources that can be obtained from nature. Alternately, glucose and xylose also can be obtained from hydrolysis of other natural biomass, such as celluloses, lignocelluloses, or xylans.

Fructose, an isomer of glucose, is a substance widely used as a sweetener in the food industry. Recently, fructose also can be used as a raw material for 5-hydroxymethylfurfural (HMF), which can be used as an intermediate of dimethylfuran (DMF) or bioplastics, such as polyethylene furanoate (PEF), etc. Further, xylulose, an isomer of xylose, also can be used as biofuel by converting to furfural due to dehydration. Additionally, xylulose prepared via an isomerization reaction of xylose is being explored as a novel sweetener.

Although a glucose isomerization reaction which industrially prepares fructose is carried out using immobilized enzymes, the use of these enzymes is not only expensive but also very sensitive to several process conditions, such as pH, temperature, etc., and therefore, there are restrictions on production environment (*Applied Biochemistry and Biotechnology*, 1990, 23: 187; *Catalysis Communications*, 2012, 29: 63). Further, it is disadvantageous in that a chromatography method which requires expensive equipments are necessarily to be used in order to separate fructose, a product, and the residual glucose, which has not been reacted upon the completion of the isomerization reaction using the enzymes. This disadvantage is also identically applied to the process of isomerizing xylose to produce xylulose.

In order to overcome these limitations, a catalyst and/or process for converting glucose to fructose and xylose to xylulose has recently been studied by using a heterogeneous catalytic process. However, at present, the production yield at the level of an enzyme process has not been achieved (*PNAS*, 2010, 107: 6164; *Applied Catalysis A: General*, 2008, 339: 21). In addition, conventional research which converts glucose to fructose, and xylose to xylulose through a heterogeneous catalytic process has failed to suggest a technique to separate the products resulted therefrom.

DISCLOSURE

Technical Problem

The present inventors have conducted extensive and intensive researches in order to find a method for preparing fructose and xylulose in high yield from biomass comprising monosaccharides, such as glucose and xylose, and to find a method for easily separating unreacted reactants and products. As a result, it was confirmed that fructose and xylulose can be prepared in high yield when an isomerization reaction is carried out using butanol as a solvent and a hydrotalcite containing magnesium as a solid base catalyst or using a zeolite containing aluminum as a solid acid catalyst; and also confirmed that unreacted reactants, glucose and xylose, and resulting products, fructose and xylulose, were easily separated when the process of cooling to a specific temperature and the process of filtering by using the difference in solubility of a reactant and a product are sequentially carried out, thereby completing the present invention.

Technical Solution

A first aspect of the present invention provides a method for preparing fructose or xylulose from biomass containing glucose or xylose, comprising: a first step of reacting the biomass containing glucose or xylose in the presence of a solid base or solid acid catalyst at 80° C. to 150° C. using butanol as a solvent, to isomerize glucose or xylose; and a second step of cooling the reaction solution obtained from the first step to 40° C. to 60° C. to crystallize unreacted glucose or xylose and then filtering the resultant to remove the unreacted glucose or xylose.

A second aspect of the present invention provides a method for preparing 5-hydroxymethylfurfural or furfural from the biomass containing glucose or xylose, comprising: a first step of reacting the biomass containing glucose or xylose in the presence of a solid base or solid acid catalyst at 80° C. to 150° C. using butanol as a solvent, to prepare fructose or xylulose by isomerizing glucose or xylose; a second step of cooling the reaction solution obtained from the first step to 40° C. to 60° C. to crystallize unreacted glucose or xylose and then filtering the resultant to remove the unreacted glucose or xylose; and a third step of adding a solid acid catalyst to the reaction solution obtained from the second step and dehydrating fructose or xylulose, to prepare 5-hydroxymethylfurfural or furfural.

A third aspect of the present invention provides a method for separating a mixture of glucose and fructose, comprising: a first step of preparing a solution comprising a mixture of glucose and fructose in butanol; and a second step of adjusting the temperature of the solution to 40° C. to 60° C. to specifically dissolve fructose, and separating glucose from the solution by filtration.

A fourth aspect of the present invention provides a method for separating a mixture of xylose and xylulose, comprising: a first step of preparing a solution comprising a mixture of xylose and xylulose in butanol; and a second step of adjusting the temperature of the solution to 40° C. to 60° C. to specifically dissolve xylulose, and separating xylose from the solution by filtration.

Hereinbelow, the present invention will be described in detail.

The present invention is based on the discovery that glucose and xylose, which are monosaccharides capable of being isomerized to provide raw materials for biofuel, exhibit large solubility differences between the isomers thereof, such as fructose and xylulose, for a butanol solvent.

Conventionally, in the process of isomerizing glucose or xylose, it was inevitable to use enzymes in order to achieve high yield. However, when using enzymes, it is impossible to exclude the effects caused by reaction conditions, such as pH and temperature. In this regard, efforts have been made to find a method to achieve high conversion rates and/or yields by using the process of an isomerization reaction which uses a chemical catalyst.

When a glucose isomerization reaction is conventionally carried out in an aqueous solution using a Sn-Beta zeolite as a solid acid catalyst, glucose conversion rate (55%) and fructose yield (32%) were achieved at a reaction temperature of 110° C. (*PNAS,* 2010, 107(10): 6164). Although it was possible to achieve relatively high fructose yield in an aqueous solution by using the technique above, the Sn-Beta zeolite cannot be massively synthesized, and therefore, such technique is difficult to be commercialized.

As another example, when a glucose isomerization reaction was carried out in an aqueous solution using a solid base catalyst of a hydrotalcite containing Mg, glucose conversion rate (41%) and fructose yield (32%) were achieved at a reaction temperature of 90° C. (*Catal. Sci. Technol.,* 2014, 4(12): 4322). It was possible in the technique above to achieve relatively high fructose yield in an aqueous solution by using a magnesium-containing hydrotalcite, the synthesis of which is relatively easy. However, there is a disadvantage in that magnesium in the catalyst of the magnesium-containing hydrotalcite is dissolved in an aqueous solution.

Additionally, as described above, when the glucose isomerization reaction is carried out in the aqueous solution, it is troublesome to separate glucose and fructose through complicated additional processes upon the completion of the reaction.

Accordingly, in the present invention, the glucose isomerization reaction was carried out not with an aqueous solution but with a butanol solvent, and as a result, it was discovered that high glucose conversion rate can be shown, as well as fructose selectivity can be kept high because the use of the butanol solvent suppresses condensation and/or decomposition reaction of glucose and fructose, generated in an aqueous solution.

Additionally, since the difference in solubility for butanol between glucose and xylose and the isomers thereof, i.e., fructose and xylulose, is large, specific components can be selectively crystallized by controlling a temperature after carrying out the isomerization reaction. As a result, it was discovered in the present invention that the reactant and product and/or the butanol solvent can be sequentially separated due to simple cooling and filtration.

For example, glucose is hardly dissolved in 1-butanol per 100 g under the condition of 50° C., but since fructose has solubility of 32 g, a 1-butanol solution comprising both unreacted glucose and a product, fructose, can be simply cooled to 50° C. after carrying out the glucose isomerization reaction at 100° C. or above. As a result, glucose having remarkably low solubility at the corresponding temperature can be selectively crystallized, thereby easily separating the glucose by filtration.

Additionally, since butanol has a boiling point higher than that of water (for example, 1-butanol has a boiling point of about 118° C. at 1 atm), the reaction temperature can be increased to at least 100° C. or higher up to 120° C. even at an atmospheric pressure. As a result, it was confirmed that the efficiency of the isomerization reaction by a chemical catalyst can be remarkably improved.

The method of the present invention for preparing fructose or xylulose from biomass comprising glucose or xylose, comprises: a first step of reacting the biomass containing glucose or xylose in the presence of a solid base or solid acid catalyst at 80° C. to 150° C. using butanol as a solvent, to isomerize glucose or xylose; and a second step of cooling the reaction solution obtained from the first step to 40° C. to 60° C. to crystallize unreacted glucose or xylose and then filtering the resultant to remove the unreacted glucose or xylose.

For example, the first step can be carried out at 80° C. to 135° C. Preferably, the first step can be carried out at 90° C. to 125° C., but is not limited thereto. When the reaction is carried out at a temperature below 80° C., it is difficult to achieve the desired level of reaction rate (i.e., conversion rate and/or yield) because the reaction is delayed. However, in consideration of the boiling point of butanol, when the reaction was carried out at a temperature exceeding 150° C., a solution, i.e., a solvent as well as a reactant and a product dissolved therein, may possibly be evaporated and disappeared. Further, the selectivity of a product may be reduced because production of other by-products in addition to the isomerization products is increased at a high temperature.

For example, the resulting product, fructose or xylulose, may be separated from the butanol solvent by additionally carrying out a third step of cooling the reaction solution obtained from the second step, that is, the butanol solution containing the product (fructose or xylulose) which is remained after the crystallization and removal of the residual glucose or xylose which is not reacted in the entire reaction mixture solution of the first step, to 10° C. to 30° C. to crystallize fructose or xylulose and then filtering to recover the fructose or xylulose. However, the method of removing the solvent from the resulting product is not limited thereto, and may be carried out using a solvent-removal method known in the art.

For example, a magnesium-containing hydrotalcite may be used for the solid base catalyst. For example, the magnesium-containing hydrotalcite may be a material which is post-treated through calcination and rehydration after being prepared by a precipitation method, but is not limited thereto.

Herein, the solid base catalyst may include magnesium in a molar ratio of 0.5 to 3.5:1 relative to the amount of aluminum contained in the solid base catalyst, but is not limited thereto.

On the other hand, an aluminum-containing zeolite may be used for the solid acid catalyst.

Herein, the solid acid catalyst may include silicon in a molar ratio of 5 to 50:1 relative to the amount of aluminum contained in the solid acid catalyst, but is not limited thereto.

In a specific exemplary embodiment of the present invention, similar to the preparation method of the present invention, fructose was prepared by reacting glucose at 120° C. for 5 hours using a butanol solvent, followed by isomerizing the same. However, instead of using a magnesium-containing hydrotalcite or an aluminum-containing zeolite, various catalysts, such as NaOH, MgO, and $Al_2O_3$, were used in the reaction. As a result, it was discovered that fructose was prepared with a high selectivity of 70% or more in the preparation method using the hydrotalcite or the zeolite according to the present invention. However, it was also discovered that when using the other above-mentioned catalysts, fructose was prepared with a selectivity thereof of below 70%.

In the preparation method of the present invention, the biomass containing glucose or xylose may be used in an amount of 1 wt % to 30 wt % relative to the amount of the butanol solvent, but is not limited thereto. However, in the case of using the biomass containing glucose or xylose, which is a reactant, at a high concentration exceeding 30 wt %, it is not completely dissolved in the butanol solvent, or the viscosity of the solution and the density of the reactant in the solution become high. Accordingly, the reactant would not sufficiently react with a catalyst, and as a result, the reactant would be remained in an unreacted state, thereby reducing the conversion rate. Conversely, when the biomass concentration is as low as below 1 wt %, the productivity would be reduced, thereby causing the efficiency of the entire process to be decreased.

Herein, the solid base or solid acid catalyst may be used in an amount of 10 wt % to 100 wt % relative to the amount of the biomass containing glucose or xylose, but is not limited thereto. However, when the proportion of the catalyst for the biomass is less than 10 wt %, the reaction rate may be slow because the reactant cannot sufficiently contact with the catalyst, and as a result, the conversion rate of biomass and the yield of product may be lowered. In addition, when the proportion of the catalyst for the biomass exceeds 100 wt %, side reactions may be increased so that the product selectivity may decrease.

For example, the butanol may be 1-butanol, 2-butanol, or isobutanol. These butanols, such as 1-butanol, 2-butanol, and isobutanol, are solvents having boiling points of about 118° C., 98° C. to 100° C., and 108° C., respectively. Therefore, these butanols increase the reaction temperature to a level equal to or higher than that of using water as a solvent, and thus the reaction efficiency may be improved. Preferably, 1-butanol having the highest boiling point and low solubility in water may be used.

Additionally, the method of the present invention for preparing 5-hydroxymethylfurfural or furfural from the biomass containing glucose or xylose, comprises: a first step of reacting the biomass containing glucose or xylose in the presence of a solid base or solid acid catalyst at 80° C. to 150° C. using butanol as a solvent, to prepare fructose or xylulose by isomerizing glucose or xylose; a second step of cooling the reaction solution obtained from the first step to 40° C. to 60° C. to crystallize unreacted glucose or xylose and then filtering the resultant to remove the unreacted glucose or xylose; and a third step of adding a solid acid catalyst to the reaction solution obtained from the second step and dehydrating fructose or xylulose, to prepare 5-hydroxymethylfurfural or furfural.

For example, the solid acid catalyst may be a Bronsted acid, a Lewis acid, or a mixed catalyst thereof. The solid acid catalyst may be selected according to the type of monosaccharide contained in the biomass used for the reaction. For example, a Bronsted acid may be used when reacting with fructose, but is not limited thereto.

For example, an ion-exchange resin type of the solid acid catalyst may be used for user's convenience, but is not limited thereto.

For example, the third step may be carried out at 50° C. to 110° C., and at 0.1 atm to 1 atm, but is not limited thereto.

Additionally, the present invention provides a method for separating a mixture of glucose and fructose, comprising: a first step of preparing a solution comprising a mixture of glucose and fructose in butanol; and a second step of adjusting the temperature of the solution to 40° C. to 60° C. to specifically dissolve fructose, and separating glucose from the solution by filtration.

The separation method of the present invention may further comprise a third step of cooling and filtering the solution obtained from the second step to 10° C. to 30° C. to crystallize fructose, thereby enabling the separation of the fructose from the butanol solvent.

Additionally, the present invention provides a method for separating a mixture of xylose and xylulose, comprising: a first step of preparing a solution comprising a mixture of xylose and xylulose in butanol; and a second step of adjusting the temperature of the solution to 40° C. to 60° C. to specifically dissolve xylulose, and separating xylose from the solution by filtration.

The separation method of the present invention may further comprise a third step of cooling and filtering the solution obtained from the second step to 10° C. to 30° C. to crystallize xylulose, thereby enabling the separation of the xylulose from the butanol solvent.

The separation method of the present invention is based on the difference in solubility between glucose and fructose, and that between xylose and xylulose. Therefore, since glucose and xylose can be selectively crystallized in the butanol solution of 40° C. to 60° C., only fructose and xylulose can be selectively dissolved. As a result, the crystallized glucose or xylose can be separated from the mixture thereof with fructose or xylulose through simple filtration.

Additionally, the separation method of the present invention can also be applied to the separation of a mixture of glucose and fructose or a mixture of xylose and xylulose, which is prepared by carrying out the isomerization reaction which uses an enzyme in an aqueous solution. For example, it is possible to apply the separation method of the present invention to separate glucose and fructose or to separate xylose and xylulose by removing water, a solvent, from an aqueous solution, followed by addition of butanol.

In the separation method of the present invention, 1-butanol, 2-butanol, or isobutanol may be used for the butanol, but is not limited thereto. For example, 1-butanol may be used since it has a lower solubility in water.

In the separation method of the present invention, the temperature of the solution in the first step may be raised to 50° C. or higher (e.g., 60° C. or higher) so that the method can be carried out to completely dissolve glucose and fructose, or xylose and xylulose in butanol, but is not limited thereto.

Advantageous Effects

The method of the present invention for preparing fructose or xylulose is carried out in a butanol solvent, and thus high glucose conversion rate can be shown, as well as fructose selectivity can be kept high because condensation or decomposition reaction of glucose and fructose, which is a side reaction easily occurring in an aqueous solution, is inhibited. Further, glucose and xylose, which are the reactants, and fructose and xylulose, which are the products, exhibit large difference in solubility for the butanol solvent. Therefore, the unreacted residual reactants and products can be easily separated from the reaction mixture solution by simple cooling and filtration after completion of the isomerization reaction.

BRIEF DESCRIPTIONS OF THE DRAWINGS

DETAILED DESCRIPTION OF THE EMBODIMENT

Hereinbelow, the present invention will be described in detail with accompanying exemplary embodiments. However, the exemplary embodiments disclosed herein are only for illustrative purposes and should not be construed as limiting the scope of the present invention.

Preparation Example 1: Preparation of Hydrotalcite Catalyst

A hydrotalcite having an Mg/Al molar ratio of 1.0 to 5.0 was prepared using precursors, $Mg(NO_3)_2 \cdot 6H_2O$ (Sigma-Aldrich, 99%) and $Al(NO_3)_3 \cdot 9H_2O$ (Sigma-Aldrich, 99%). Specifically, $Mg(NO_3)_2 \cdot 6H_2O$ (12.88 g, 0.05 mol) and $Al(NO_3)_3 \cdot 9H_2O$ (9.37 g, 0.025 mol) were dissolved in deionized water (200 mL). An aqueous solution (100 mL) of $NaHCO_3$ (Sigma-Aldrich, 99%, 4.20 g, 0.05 mol) was added dropwise to the obtained mixture solution, and then gradually precipitated. During the co-precipitation, the pH of the mixture solution was maintained at 10.0 by adding an aqueous solution of 2.0 M NaOH (Sigma-Aldrich, 99%). After the precipitation, the precipitate formed was aged at 100° C. for 24 hours. The aged mixture was filtered, and then washed several times with deionized water until the pH of the filtrate became neutral. The filtered solid was dried overnight at 120° C. using an oven, and then calcined in an air current at 450° C. for 10 hours. The calcined sample was poured into deionized water (200 mL), and then treated under nitrogen flow (50 mL/minute) at 50° C. for 24 hours for rehydration. The produced solid was filtered and dried overnight in an oven at 80° C., thereby obtaining a magnesium-containing hydrotalcite (Mg/Al=2.0). Further, the hydrotalcite, the Mg/Al ratio of which was adjusted from 1.0 to 5.0 by controlling the usage of $Mg(NO_3)_2 \cdot 6H_2O$ and $Al(NO_3)_3 \cdot 9H_2O$, was additionally synthesized.

Figure 1:
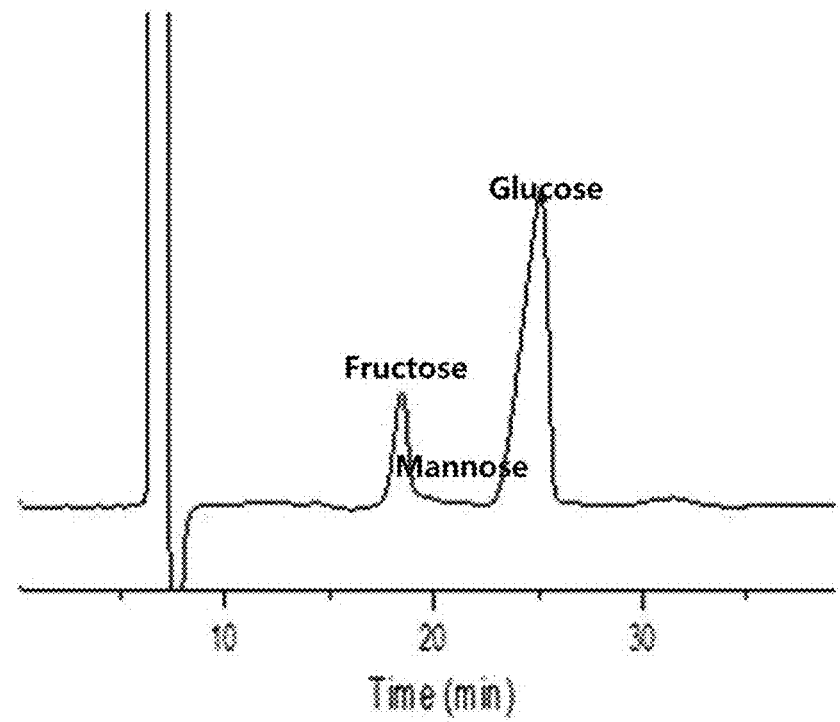
FIG. 1 is a graph showing the result of liquid chromatography analysis for the reaction preparing fructose from glucose in butanol using the hydrotalcite catalyst according to an exemplary embodiment (Example 1) of the present invention.

Example 1: (1) Preparation of Fructose from Glucose According to Reaction Temperature After glucose (1.0 g) was mixed with 1-butanol (10 g) and a hydrotalcite (0.5 g, Mg/Al=2.0), the resultant was heated to 95° C., and then reacted for 5 hours, thereby preparing fructose. After completion of the reaction, the hydrotalcite was separated from the reaction mixture solution by filtration. The obtained reaction mixture solution was then analyzed using a liquid chromatography, and the result is shown in FIG. 1. Herein, the glucose conversion rate was 22%; the fructose yield was 20%; and the fructose selectivity was 91%.

Example 2: (2) Preparation of Fructose from Glucose According to Reaction Temperature Fructose was prepared in the same manner as in Example 1, except that the reaction temperature was raised to 103° C. instead of 95° C. Herein, the glucose conversion rate was 35%; the fructose yield was 31%; and the fructose selectivity was 89%.

Example 3: (3) Preparation of Fructose from Glucose According to Reaction Temperature Fructose was prepared in the same manner as in Example 1, except that the reaction temperature was raised to 120° C. instead of 95° C. Herein, the glucose conversion rate was 62%; the fructose yield was 51%; and the fructose selectivity was 82%.

Example 4: Preparation of Fructose from Glucose According to Reaction Time

Fructose was prepared in the same manner as in Example 3, except that the reaction time was increased from 5 hours to 10 hours. Herein, the glucose conversion rate was 74%; the fructose yield was 57%; and the fructose selectivity was 77%.

Example 5: (1) Preparation of Fructose from Glucose According to Ratio of Mg in Catalyst Fructose was prepared in the same manner as in Example 3, except that a hydrotalcite having an Mg/Al ratio of 1.5 was used instead of a hydrotalcite having an Mg/Al ratio of 2.0. Herein, the glucose conversion rate was 59%; the fructose yield was 49%; and the fructose selectivity was 83%.

Example 6: (2) Preparation of Fructose from Glucose According to Ratio of Mg in Catalyst Fructose was prepared in the same manner as in Example 3, except that a hydrotalcite having an Mg/Al ratio of 3.0 was used instead of a hydrotalcite having an Mg/Al ratio of 2.0. Herein, the glucose conversion rate was 66%; the fructose yield was 46%; and the fructose selectivity was 70%.

Example 7: (3) Preparation of Fructose from Glucose According to Ratio of Mg in Catalyst Fructose was prepared in the same manner as in Example 3, except that MgO was used instead of a hydrotalcite (Mg/Al=2.0) as the catalyst. After the reaction, MgO was separated by filtration, and the separated reaction mixture solution was analyzed using a liquid chromatography. Herein, the glucose conversion rate was 47%; the fructose yield was 34%; and the fructose selectivity was 72%.

Example 8: Preparation of Fructose from Glucose by Using H-Beta Catalyst

Fructose was prepared in the same manner as in Example 3, except that a zeolite was used instead of a hydrotalcite (Mg/Al=2.0) as the catalyst. After the reaction, the H-Beta zeolite was separated by filtration, and the separated reaction mixture solution was analyzed using a liquid chromatography. Herein, the glucose conversion rate was 41%; the fructose yield was 33%; and the fructose selectivity was 80%.

Example 9: Preparation of Fructose from Glucose by Using H-ZSM-5 Catalyst

Fructose was prepared in the same manner as in Example 3, except that an H-ZSM-5(Si/Al=23) zeolite was used instead of a hydrotalcite (Mg/Al=2.0) as the catalyst. After the reaction, the H-ZSM-5 zeolite was separated by filtration, and the separated reaction solution was analyzed using a liquid chromatography. Herein, the glucose conversion rate was 39%; the fructose yield was 28%; and the fructose selectivity was 72%.

Example 10: Separation of Glucose and Fructose

Figure 2:
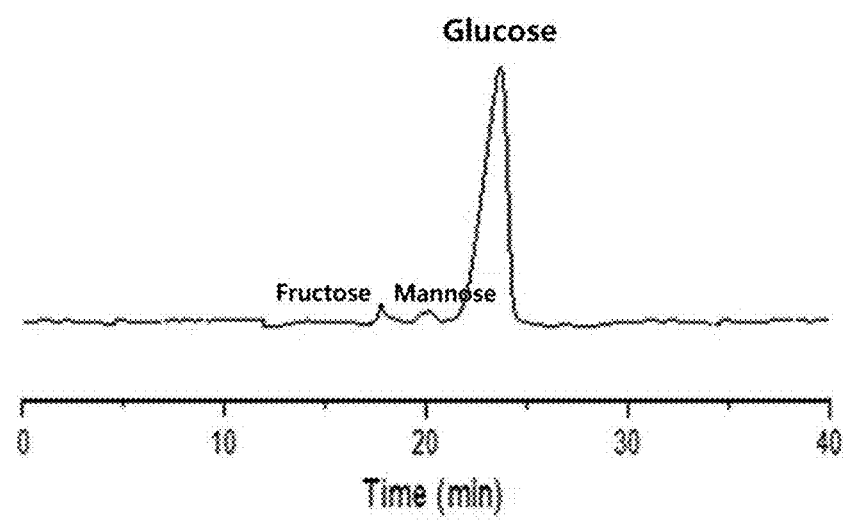
FIG. 2 is a graph showing the result of liquid chromatography analysis for unreacted glucose, which was separated by cooling and filtration after the fructose preparation process according to the present invention.

The glucose/fructose/butanol mixture obtained from Example 3 was cooled to 45° C., and only the unreacted glucose was selectively crystallized. The glucose crystallized through the process above was separated from the fructose/butanol solution by filtration together with the solid catalyst used in the reaction. The separated glucose crystals were analyzed using a liquid chromatography, and the result is shown in FIG. 2. As a result, the glucose content in the separated crystals was 95% or above.

Example 11: Separation of Fructose and Butanol

Figure 3:
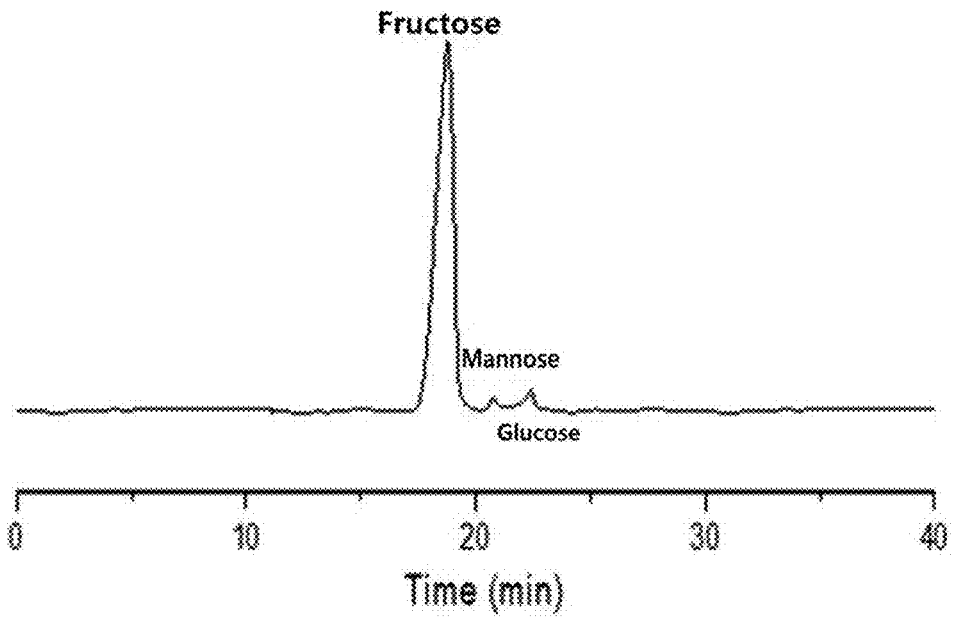
FIG. 3 is a graph showing the result of liquid chromatography analysis for fructose separated by recooling and filtering the reaction mixture, in which unreacted glucose was removed after the fructose preparation process according to the present invention.

The fructose/butanol mixture solution obtained from Example 10 was cooled to room temperature to crystallize fructose. The fructose crystallized through the process above was separated from the butanol solution by filtration. The separated fructose crystals were analyzed using a liquid chromatography, and the result is shown in FIG. 3. As a result, the fructose content in the separated crystals was 99% or above.

Figure 4:
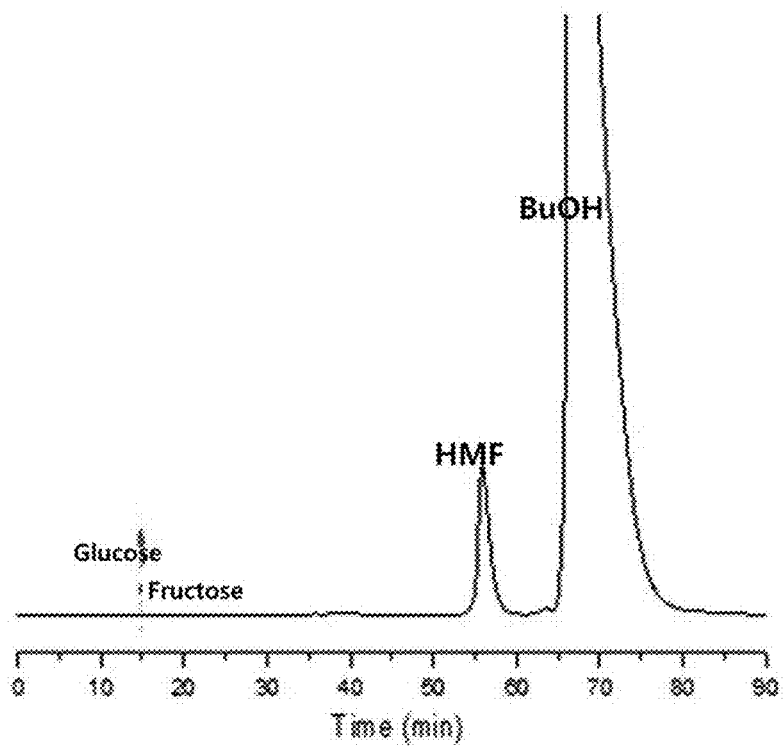
FIG. 4 is a graph showing the result of liquid chromatography analysis for the resulting product, hydroxymethylfurfural, which was converted from the fructose prepared according to the method of the present invention.

Example 12: Preparation of Hydroxymethylfurfural from Fructose 5-hydroxymethylfurfural was prepared through a dehydration reaction which uses the fructose obtained from Example 11 as the reactant. Specifically, fructose (4.2 g) and butanol (23.8 g) were mixed with Amberlyst-15 (0.28 g). Thereafter, the resultant was heated to 100° C., and reacted for 5 hours. The product obtained after the reaction was analyzed using a liquid chromatography, and the result is shown in FIG. 4. As a result, the fructose conversion rate was 100%; and the yield of 5-hydroxymethylfurfural was 92%.

Example 13: Preparation of Xylulose from Xylose

The reaction was carried out in the same manner as in Example 2 to prepare xylulose, except that xylose was used instead of glucose. Herein, the xylose conversion rate was 36%; the xylulose yield was 30%; and the xylulose selectivity was 83%.

Example 14: Preparation of Fructose from Glucose in 2-Butanol Solvent

Glucose (1.0 g) was mixed with 2-butanol (10 g) and a hydrotalcite (0.5 g, Mg/Al=2.0), and then heated to 100° C. Thereafter, the resultant was reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 25%; the fructose yield was 22%; and the fructose selectivity was 88%.

Comparative Example 1: Preparation of Fructose from Glucose Using Solid Base Catalyst in Water Solvent Glucose (1.0 g) was mixed with water (10 g) and a hydrotalcite (0.5 g, Mg/Al=2.0). Thereafter, the resultant was reacted under reflux conditions for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 54%; the fructose yield was 30%; and the fructose selectivity was 56%.

On the other hand, since glucose and fructose have very high solubility in water at 909 g/L (@ 25° C.) and 3,750 g/L (@ 20° C.) respectively, the glucose/fructose prepared through the process above could not be separated from water even when the glucose/fructose were cooled to room temperature.

Comparative Example 2: Preparation of Fructose from Glucose Using Solid Acid Catalyst in Water Solvent Fructose was prepared in the same manner as in Comparative Example 1, except that an H-Beta (Si/Al=25) zeolite was used instead of a hydrotalcite (Mg/Al=2.0) as the catalyst. Herein, the glucose conversion rate was 54%; the fructose yield was 23%; and the fructose selectivity was 43%.

Comparative Example 3: Preparation of Fructose from Glucose Using Solid Acid Catalyst in Water Solvent Fructose was prepared in the same manner as in Comparative Example 1, except that an H-ZSM-5(Si/Al=23)

zeolite was used instead of a hydrotalcite (Mg/Al=2.0) as the catalyst. Herein, the glucose conversion rate was 48%; the fructose yield was 20%; and the fructose selectivity was 42%.

Comparative Example 4: Preparation of Fructose from Glucose in DMF Solvent

Glucose (1.0 g) was mixed with dimethylformamide (DMF; 10 g) and a hydrotalcite (0.5 g, Mg/Al=2.0). Thereafter, the resultant was heated to 130° C., and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 100%; the fructose yield was 1%; and the fructose selectivity was 1%.

Comparative Example 5: Preparation of Fructose from Glucose in DMSO Solvent

Glucose (1.0 g) was mixed with dimethyl sulfoxide (DMSO; 10 g) and a hydrotalcite (0.5 g, Mg/Al=2.0). Thereafter, the resultant was heated to 120° C., and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 99%; the fructose yield was 4%; and the fructose selectivity was 4%.

Comparative Example 6: Preparation of Fructose from Glucose in γ-Valerolactone Solvent Glucose (1.0 g) was mixed with γ-valerolactone (10 g) and a hydrotalcite (0.5 g, Mg/Al=2.0). Thereafter, the resultant was heated to 130° C., and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 93%; the fructose yield was 5%; and the fructose selectivity was 5%.

Comparative Example 7: Preparation of Fructose from Glucose by Using NaOH Catalyst Fructose was prepared in the same manner as in Example 3, except that NaOH (0.005 g) was used instead of a hydrotalcite (Mg/Al=2.0) as the catalyst. After the reaction, the mixture solution was analyzed using a liquid chromatography. Herein, the glucose conversion rate was 54%; the fructose yield was 37%; and the fructose selectivity was 68%.

Comparative Example 8: Preparation of Fructose from Glucose by Using Al$_2$O$_3$ Catalyst Fructose was prepared in the same manner as in Example 3, except that Al$_2$O$_3$ was used instead of a hydrotalcite (Mg/Al=2.0) as the catalyst. After the reaction, Al$_2$O$_3$ was separated by filtration, and the separated reaction mixture solution was analyzed using a liquid chromatography. Herein, the glucose conversions rate was 24%; the fructose yield was 14%; and the fructose selectivity was 58%.

Comparative Example 9: Preparation of Fructose from Glucose by Using Solid Base Catalyst in Methanol Solvent Glucose (1.0 g) was mixed with methanol (10 g) and a hydrotalcite (0.5 g, Mg/Al=2.0). Thereafter, the resultant was heated to 120° C. in a pressurized reactor (about 6 atm), and reacted for 5 hours to prepare fructose. After the reaction, the hydrotalcite was separated from the reaction mixture solution by filtration. The obtained reaction mixture solution was analyzed using a liquid chromatography. Herein, the glucose conversion rate was 61%; the fructose yield was 42%; and the fructose selectivity was 69%.

Thereafter, attempts were made in order to separate unreacted glucose and fructose, the product, by cooling. However, since glucose and fructose have very high solubility in methanol at 31.6 g/L (@ 40° C.) and 229.7 g/L (@ 40° C.) respectively, the glucose/fructose prepared in the methanol solvent through the process above had difficulty in selectively crystallizing only glucose even when the glucose/fructose were cooled to 40° C.

Comparative Example 10: Preparation of Fructose from Glucose by Using Solid Base Catalyst in Ethanol Solvent Glucose (1.0 g) was mixed with ethanol (10 g) and a hydrotalcite (0.5 g, Mg/Al=2.0). Thereafter, the resultant was heated to 120° C. in a pressurized reactor (about 4 atm), and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 62%; the fructose yield was 40%; and the fructose selectivity was 65%.

Thereafter, attempts were made in order to separate unreacted glucose and fructose, the product, by cooling. However, since glucose and fructose still have high solubility in ethanol at 4.21 g/L (@ 40° C.) and 36.3 g/L (@ 40° C.) respectively, the glucose/fructose prepared in the ethanol solvent through the process above had difficulty in selectively crystallizing only glucose even when the glucose/fructose were cooled to 40° C.

Comparative Example 11: Preparation of Fructose from Glucose by Using Solid Base Catalyst in 1-Pentanol Solvent Glucose (1.0 g) was mixed with 1-pentanol (10 g) and a hydrotalcite (0.5 g, Mg/Al=2.0). Thereafter, the resultant was heated to 120° C., and reacted for 5 hours to prepare fructose. After completion of the reaction, the hydrotalcite was separated from the reaction mixture solution by filtration. The obtained reaction mixture was analyzed using a liquid chromatography. Herein, the glucose conversion rate was 37%; the fructose yield was 29%; and the fructose selectivity was 78%.

Comparative Example 12: Preparation of Fructose from Glucose by Using Solid Base Catalyst in 1-Pentanol Solvent Glucose (1.0 g) was mixed with 1-pentanol (10 g) and a hydrotalcite (0.5 g, Mg/Al=2.0). Thereafter, the resultant was heated to 140° C., and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 72%; the fructose yield was 39%; and the fructose selectivity was 54%.

Comparative Example 13: Preparation of Fructose from Glucose by Using Solid Base Catalyst in 1-Hexanol Solvent Glucose (1.0 g) was mixed with 1-hexanol (10 g) and a hydrotalcite (0.5 g, Mg/Al=2.0). Thereafter, the resultant was heated to 120° C., and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 32%; the fructose yield was 23%; and the fructose selectivity was 72%.

Comparative Example 14: Preparation of Fructose from Glucose by Using Solid Base Catalyst in 1-Hexanol Solvent Glucose (1.0 g) was mixed with 1-hexanol (10 g) and a hydrotalcite (0.5 g, Mg/Al=2.0). Thereafter, the resultant was heated to 160° C., and reacted for 5 hours to prepare fructose. After completion of the reaction, the hydrotalcite was separated from the reaction mixture solution by filtration. The obtained reaction mixture solution was analyzed using a liquid chromatography. Herein, the glucose conversion rate was 86%; the fructose yield was 41%; and the fructose selectivity was 48%.

As shown in Example 3 and Comparative Examples 9 and 10, it was confirmed that the conversion to fructose with higher yield and selectivity was made possible using butanol as a solvent at a lower pressure (e.g., even without pressure application), compared to the case of using methanol or ethanol as the solvent. In addition, since the reaction could be carried out even at atmospheric pressure, it was also advantageous to separate unreacted glucose and fructose, the product, after completion of the reaction.

Additionally, as shown in Comparative Examples 11 to 14, there was a drawback in that the glucose conversion rate and fructose yield were low due to the low solubility of glucose at the same reaction temperature when using 1-pentanol and 1-hexanol as solvents, compared to the case of using a butanol solvent. Further, although the glucose conversion rate could be increased when the reaction temperature was raised so as to increase the solubility of glucose, the fructose selectivity was rather lowered as other side reactions increased, in addition to the isomerization reaction.

Overall, it was confirmed that when a glucose isomerization reaction was carried out in a butanol solvent, fructose with higher yield and selectivity can be prepared, compared to glucose isomerization reactions using other solvents including organic solvents, such as water, etc. Further, it was confirmed that when a glucose isomerization reaction was carried out using a hydrotalcite as a catalyst in a butanol solvent, fructose with higher yield and selectivity can be prepared, compared to glucose isomerization reactions using other catalysts, such as NaOH, MgO, and various zeolites. Furthermore, in the case of preparing fructose through a glucose isomerization reaction in a butanol solvent, it was found that glucose and fructose were sequentially crystallized at mutually different temperatures via a simple cooling process, based on the solubility difference of the reactant and product to butanol. Therefore, the products and extra reactants which were not reacted could sequentially be separated by filtration. That is, after conducting the isomerization reaction at a high temperature of about 120° C., glucose which was crystallized by primary cooling at 45° C. was filtered to separate the unreacted glucose, which is the residual reactant, from the reaction mixture solution. Thereafter, the filtrate was secondarily cooled to a room temperature to crystallize fructose, and thus fructose, the resulting product, could be easily separated from the butanol solvent by filtration.

The invention claimed is:
1. A method for preparing fructose or xylulose from biomass containing glucose or xylose, comprising:
   a first step of reacting the biomass containing glucose or xylose in the presence of a solid base or solid acid catalyst at 80° C. to 150° C. using butanol as a solvent, to isomerize glucose or xylose; and
   a second step of cooling the reaction solution obtained from the first step to 40° C. to 60° C. to crystallize unreacted glucose or xylose and then filtering the resultant to remove the unreacted glucose or xylose.
2. The method of claim 1, which further comprises a third step of cooling the reaction solution obtained from the second step to 10° C. to 30° C. to crystallize fructose or xylulose and then filtering to recover the fructose or xylulose.
3. The method of claim 1, wherein the solid base catalyst is a hydrotalcite containing magnesium.
4. The method of claim 3, wherein the solid base catalyst comprises magnesium in a molar ratio of 0.5 to 3.5:1 relative to the amount of aluminum contained in the solid base catalyst.
5. The method of claim 1, wherein the solid acid catalyst is a zeolite containing aluminum.
6. The method of claim 5, wherein the solid acid catalyst comprises silicon in a molar ratio of 5 to 50:1 relative to the amount of aluminum contained in the solid acid catalyst.
7. The method of claim 1, wherein the biomass comprising glucose or xylose is used in an amount of 1 wt % to 30 wt % relative to the amount of the butanol solvent.
8. The method of claim 1, wherein the solid base or solid acid catalyst is used in an amount of 10 wt % to 100 wt % relative to the amount of the biomass containing glucose or xylose.
9. The method of claim 1, wherein the butanol is 1-butanol, 2-butanol, or isobutanol.
10. A method for preparing 5-hydroxymethylfurfural or furfural from the biomass containing glucose or xylose, comprising:
   a first step of reacting the biomass containing glucose or xylose in the presence of a solid base or solid acid catalyst at 80° C. to 150° C. using butanol as a solvent, to prepare fructose or xylulose by isomerizing glucose or xylose;
   a second step of cooling the reaction solution obtained from the first step to 40° C. to 60° C. to crystallize unreacted glucose or xylose and then filtering the resultant to remove the unreacted glucose or xylose; and
   a third step of adding a solid acid catalyst to the reaction solution obtained from the second step and dehydrating fructose or xylulose, to prepare 5-hydroxymethylfurfural or furfural.
11. The method of claim 10, wherein the third step is carried out at 50° C. to 110° C. at 0.1 atm to 1 atm.

12. A method for separating a mixture of glucose and fructose, comprising:
- a first step of preparing a solution comprising a mixture of glucose and fructose in butanol; and
- a second step of adjusting the temperature of the solution to 40° C. to 60° C. to specifically dissolve fructose, and separating glucose from the solution by filtration.

13. The method of claim 12, which further comprises a third step of cooling and filtering the solution obtained from the second step to 10° C. to 30° C. to crystallize fructose.

14. A method for separating a mixture of xylose and xylulose, comprising:
- a first step of preparing a solution comprising a mixture of xylose and xylulose in butanol; and
- a second step of adjusting the temperature of the solution to 40° C. to 60° C. to specifically dissolve xylulose, and separating xylose from the solution by filtration.

15. The method of claim 14, wherein the method further comprises a third step of cooling and filtering the solution obtained from the second step to 10° C. to 30° C. to crystallize xylulose.

16. The method of claim 12, wherein the butanol is 1-butanol, 2-butanol, or isobutanol.

17. The method of claim 14, wherein the butanol is 1-butanol, 2-butanol, or isobutanol.

* * * * *